United States Patent [19]

Cueman

[11] Patent Number: 4,826,770
[45] Date of Patent: May 2, 1989

[54] CARBON DIOXIDE MONITORING OF COMPOSITES

[75] Inventor: Michael K. Cueman, Schenectady, N.Y.

[73] Assignee: General Electric Company, Schenectady, N.Y.

[21] Appl. No.: 100,398

[22] Filed: Sep. 24, 1987

[51] Int. Cl.$^4$ .................. G01N 31/00; G01N 17/00; G01N 30/02; G01N 31/12
[52] U.S. Cl. ......................... 436/6; 422/53; 422/89; 422/78
[58] Field of Search .............. 422/53, 78, 68, 89; 436/6, 155, 157, 2, 53; 156/620; 73/61.2

[56] References Cited

U.S. PATENT DOCUMENTS

| | | | |
|---|---|---|---|
| 4,137,047 | 1/1979 | Kim | 436/6 |
| 4,217,544 | 8/1980 | Schmidt | 436/6 |
| 4,253,846 | 3/1981 | Smythe et al. | 436/53 |
| 4,375,451 | 3/1983 | Seligman et al. | 422/53 |
| 4,552,722 | 11/1985 | Fritscher et al. | 436/6 |

*Primary Examiner*—Benoit Castel
*Assistant Examiner*—T. J. Wallen
*Attorney, Agent, or Firm*—Donald R. Campbell; James C. Davis, Jr.; Paul R. Webb, II

[57] ABSTRACT

Coated carbon composite parts to be tested for oxidation resistance are heated in a closed oven filled with an oxidizing atmosphere. During the heat cycle the carbon dioxide content of the oven atmosphere is measured by an analyzer such as a gas chromatograph. These measurements on the amount of $CO_2$ emitted by the part provide information on the onset of oxidative failure. It forms a nondestructive test when detection of excessive carbon dioxide concentration is used to reduce the temperature and flood the oven with inert gas so the part may be saved and reprocessed. This technique can be combined with conventional weight measurements before and after oxidation to identify the part constituent, carbon composite or protective coating, that failed.

10 Claims, 2 Drawing Sheets

CARBON DIOXIDE MONITORING OF COMPOSITES

BACKGROUND OF THE INVENTION

This invention relates to a method of evaluating the quality of carbon composite parts, and especially to improvements in testing the oxidation resistance of composite materials at high temperatures.

Composite materials made of graphite fibers embedded in a carbon matrix have excellent high temperature strength characteristics and are potentially useful in jet engines. They may be fabricated into light weight structures for the sections of engines that must withstand operating temperatures of 2000° C. and more. This material retains its strength at much higher temperatures than conventional composites as long as it is protected from the oxygen in air; it burns away if exposed to oxygen at the desired operating temperature. Practical carbon composite parts must be covered with protective coatings which inhibit this destructive oxidation. The oxidation resistance of coated composite parts may be further enhanced by incorporating antioxidants, typically boron components, in the bulk material.

Both the initial selection of a protection system and subsequent verification of its application to individual parts hinges on the development of an adequate method of evaluating the oxidation of coated carbon composite samples. Traditionally the effectiveness of a given antioxidation system has been evaluated by the destructive testing of small coupons in a gravimetric oven. The sample is heated for many hours in an oxidizing atmosphere and its progressive weight loss is recorded. As carbon combines with oxygen to form carbon dioxide, the material loses carbon and its strength decreases. Those samples that lose weight are judged to be unacceptable. Such a test takes a long time, sometimes days, and may severely damage the part.

SUMMARY OF THE INVENTION

An object of the invention is to provide a sensitive, nondestructive test of the oxidation resistance of composite materials and coated carbon composite parts at high temperatures.

Another object is to augment traditional gravimetric evaluations of oxidation resistance and permit the experimentalist to distinguish between bulk carbon oxidation and coating oxidation. This potentially destructive test provides information useful in process optimization.

This invention recognizes that the direct measurement of carbon dioxide emission by the coated carbon composite part provides an alternative and improved way of evaluating oxidation resistance and part quality. It can form the basis of a nondestructive test because it enjoys fundamental sensitivity and selectivity advantages. The routine availability of analytical chemistry instrumentation which can accurately quantify minute traces of carbon dioxide even in the presence of large amounts of similar compounds enhances the practicality of the technique.

The method of nondestructively testing the oxidation resistance at high temperatures of such carbon composite parts having a protective coating, briefly stated, comprises heating the part in an enclosed oxidizing atmosphere to predetermined temperatures; monitoring said atmosphere during the heat cycle and measuring any carbon dioxide emitted by the part; and detecting a carbon dioxide concentration higher than an acceptable amount that indicates the part has unsatisfactory oxidation resistance. A further feature is that as soon as unacceptable amounts of carbon dioxide are detected the temperature is reduced and the part is flooded with inert gas to prevent further damage so it can be reprocessed.

Another aspect of the invention is that the part to be evaluated is heated according to a temperature schedule, say to well below the expected operating temperature, in a sealed oven filled with a controlled oxidizing atmosphere, either pure oxygen or a mixture of oxygen and inert gas. Small samples of the oven atmosphere are collected and analyzed for the amount of carbon dioxide produced by the part. It is determined that there is unsatisfactory oxidation resistance upon measuring a carbon dioxide concentration higher than that for acceptable parts. The oven sample is analyzed with a gas chromatograph, mass spectrometer, or infrared detector, the first being preferred. A further feature is that other emissions from the part may be detected and measured by the instrument, such as boron containing gas if the composite has been treated with boron based inhibitors.

Yet another aspect of the invention is that the carbon dioxide measurements may be combined with weight change measurements, made before and during the heat cycle, to determine the mode of failure and whether the source of the carbon dioxide is the bulk carbon or the protective coating. The latter is commonly silicon carbide. A gain in weight of the part, as opposed to the usual loss in weight because carbon has decomposed, is an indication that the coating has reacted to produce silicon dioxide and carbon dioxide. This potentially destructive evaluation provides much more information on composite performance.

DETAILED DESCRIPTION OF THE INVENTION

Figure 1:
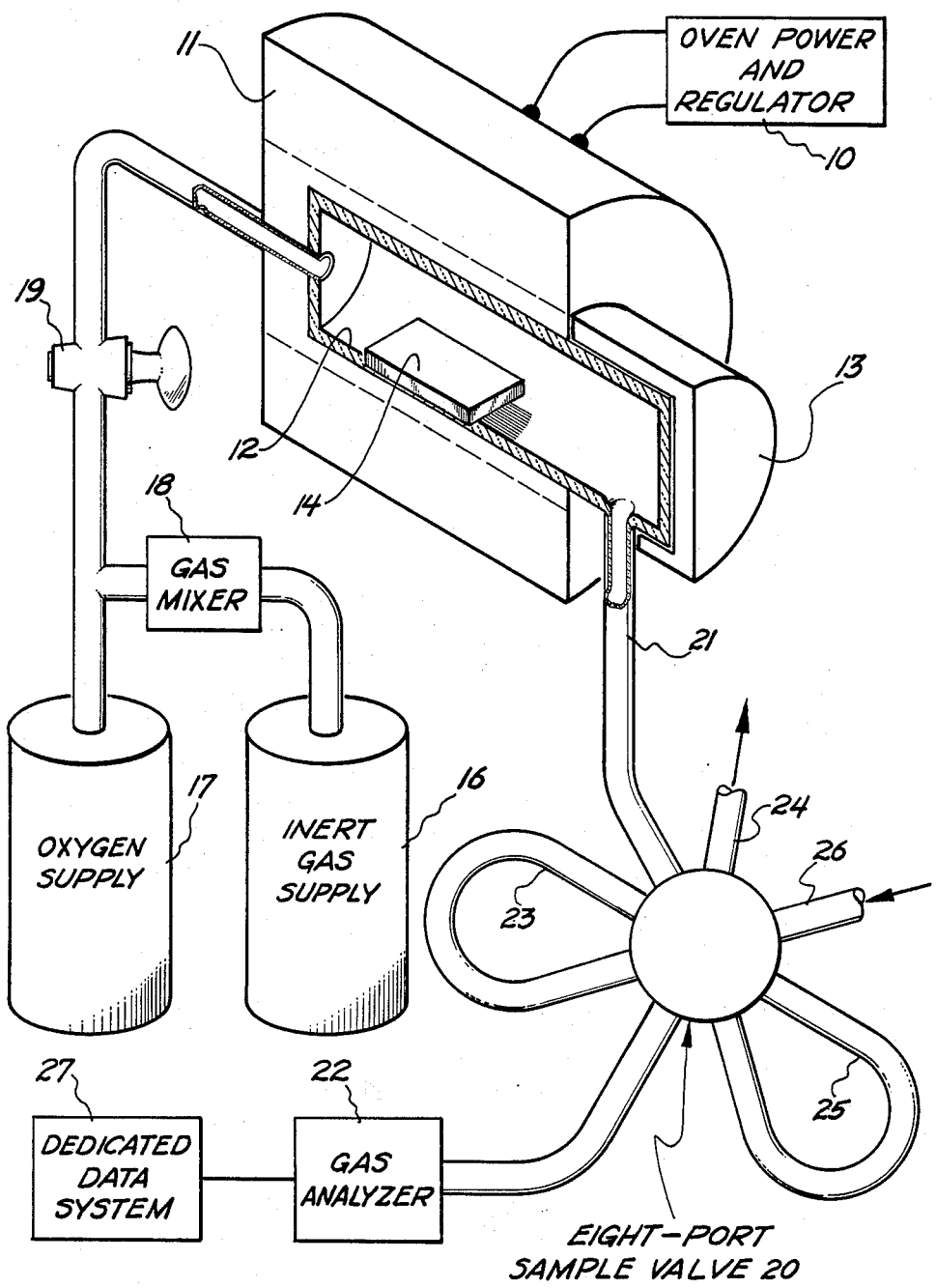
FIG. 1 is a system diagram of apparatus to heat a carbon composite part in a controlled oxidizing atmosphere and measure carbon dioxide emission from the part.

The apparatus shown in FIG. 1 may be assembled from conventional components and is used to nondestructively test the oxidation resistance of coated carbon composite parts. A small oxidation stress may be applied to production parts without either shortening their service life or affecting their suitability for reprocessing steps. The composite material is comprised of structured carbon fiber, such as graphite, in a matrix of disordered carbon, and the protective coating is typically silicon carbide. Oxygen reacts with carbon to form carbon dioxide and with silicon carbide to form silicon dioxide (quartz) and carbon dioxide. Some of the defects which occur are that thermal cycling develops a crack in the coating, whereby oxygen can attack the carbon, and that the coating has gaps in it. This test measures the amount of carbon dioxide emitted by the part without regard to the source.

The apparatus has a sealed oven with a thermostatically controlled heater, a gas supply, and an instrument to measure the amount of carbon dioxide gas that is produced when carbon composite parts are heated in the oven. In FIG. 1, an oven power and regulator unit 10 controls an electrically heated oven 11 having a quartz liner 12. A ground quartz plug 13 seals the oven chamber to prevent the introduction of atmospheric carbon dioxide. The quartz liner is chosen to prevent carbon dioxide production by the apparatus itself; other non-oxidizing materials like stainless steel or ceramics could also be used for the construction of oven walls. The composite part 14 to be inspected is placed inside the quartz lined reaction chamber.

The oven atmosphere is a mixture of oxygen and, optionally, inert gases such as helium. The gas supply does not include any carbon dioxide. The ratio of oxygen to inert gas is experimentally chosen to optimize the detection of carbon dioxide without damaging the test parts. Oxygen and inert gas supplies 16 and 17 are provided and a gas mixer 18 determines the proportion of each fed to a valve 19 and hence to the oven inlet. Oxidation tests have been run with the composite sample 14 covered in pure oxygen, while the helium was used to flood the chamber after each measurement series and protect the sample from further oxidation during slow cooling of the oven.

The carbon dioxide content of the oven atmosphere can be monitored by a number of devices including gas chromatographs, mass spectrometers, and infrared detectors. A gas chromatographic system is preferred and is illustrated. Small volumes of oven atmosphere are collected with a chromatographer's eight port sampling valve 20. This device is connected between an oven sample line 21 and the carrier gas circuit of the gas chromatograph or other gas analyzer 22. A small amount of oven atmosphere is collected in a first sample loop 23 and the excess passes out through a vent 24. The small volume of oven atmosphere already collected in a second sample loop 25 is moved into the chromatograph by carrier gas fed through line 26. A handle on sample valve 20 interchanges these two loops 23 and 25. The carbon dioxide in the samples of oven atmosphere is separated in the chromatographic column and introduced into the detector system of the instrument. The detector, which can use thermal conductivity, ultrasonic velocity, infrared absorption, or other principles, produces a signal proportional to the amount of carbon dioxide present in the sample. This signal is recorded and analyzed in a dedicated data processing system 27. To perform a nondestructive evaluation of the oxidation resistance of a coated carbon composite part, the composite sample is heated to experimentally determined temperatures well below the minimum operating temperature of 2000° C. while the oven 11 is flooded with a known concentration of oxygen or mixture of oxygen and inert gas. The carbon dioxide content of the oven atmosphere is measured at regular intervals during the heat cycle using the gas analyzer 22. When the composite part 14 being inspected begins to emit more carbon dioxide than is acceptable and exceeds the amount emitted by known acceptable parts, the oven is immediately flooded with inert gas and its temperature is reduced. This prevents unnecessary damage to the composite part 14, which has been determined to have unsatisfactory oxidation resistance and can be removed for reprocessing or other corrective actions.

This method is made practical by the routine availability of the already mentioned analytical chemistry instrumentation which can accurately quantify minute traces of carbon dioxide even in the presence of large amounts of other similar compounds. A rugged, inexpensive gas chromatograph equipped with a thermal conductivity detector can easily detect a fraction of a microgram of carbon as carbon dioxide in a milliliter volume of gas. Only slightly more elaborate chromatographs equipped with capillary columns and more specialized detectors can extend this sensitivity to at least another order of magnitude. With a reasonably well fitted oven for heating parts, the instrument can measure milligram carbon loss in kilogram samples. The equally important selectivity of the gas chromatograph permits accurate measurement of sample carbon loss even when the sample weight is simultaneously changing because of the evaporation of latent moisture or other competing chemical reactions. In fact, if these competing mechanisms produce volatile end products, they can be simultaneously measured by the same chromatograph which senses the carbon dioxide from the main carbon loss reaction. For example, it is easy to measure both the carbon dioxide and carbon monoxide coming from a composite test.

An extension of the fundamental method is to not limit the sensing of emissions to carbon dioxide, but to measure other fumes given off by composite part 14. If the carbon composite material is treated with a boron based oxidation inhibitor, the presence of a boron containing gas in the oven atmosphere signifies a crack in the protective coating. There may be other coating constituents to optimize the system. A multilayer coating may, for instance, comprise three layers of silicon carbide, borosilicate glass, and silicon carbide, and the second layer may emit a gas upon oxidizing. The concentration of these other gases in the sampled oven atmosphere is measured and provides more information with which to evaluate oxidation resistance.

The fundamental technique of carbon dioxide measurements of the oven atmosphere can also be combined with conventional measurements of composite sample weight before and after oxidation to identify the constituent of the sample which is oxidizing, the carbon material or the silicon carbide coating. The oxidation of this mixed system can be modeled with two chemical equations:

$$C + O_2 \rightarrow CO_2$$

$$SiC + 2O_2 \rightarrow CO_2 + SiO_2$$

The pure carbon reaction gives off a gas and causes the sample to lose weight. The silicon carbide reaction gives off carbon dioxide gas but it also leaves a heavy silicon dioxide modecule on the part surface. It causes a net weight gain for the part. Silicon dioxide is quartz which has good high temperature properties. Both reactions are needed to understand why some samples get lighter when heated while others get heavier. When carbon dioxide measurement is combined with weight change measurement, there is sufficient data to quantitate both equations in this two reaction model of the composite. The additional information can be used to identify the mode of failure and the weak part of the composite system.

Figure 2:
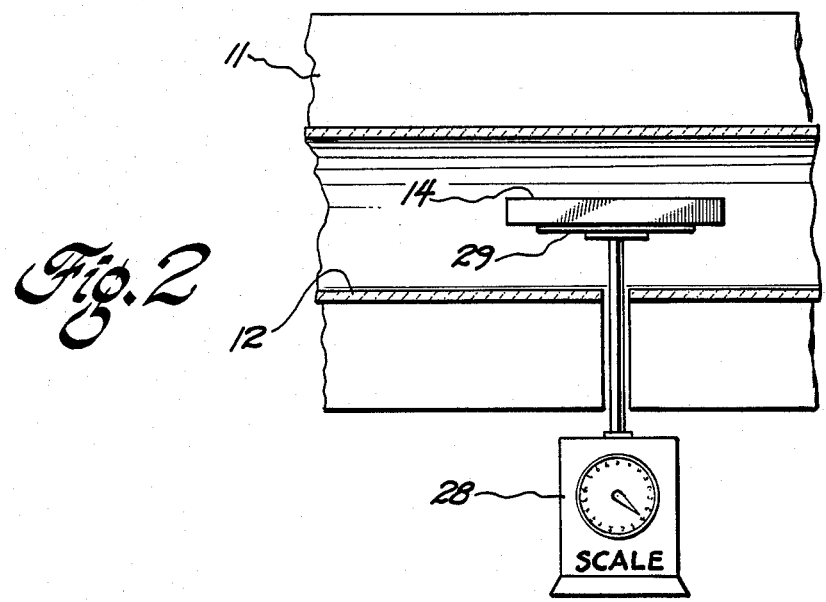
FIG. 2 shows a modification of the thermostatically controlled, sealed oven to weigh the composite sample during the heating cycle.

The modification of the electrically heated, sealed oven 11 shown in FIG. 2 permits the composite part 14 to be weighed before and during the heat cycle. The gravimetric oven has an exteriorly readable scale 28 whose platform 29 is inside the quartz lined reaction chamber and on which the part 14 being inspected rests. The part weight is measured at selected intervals as the oven temperature is increased. Alternatively, the part is weighed before putting it into the oven and immediately after taking it out.

Figure 3:
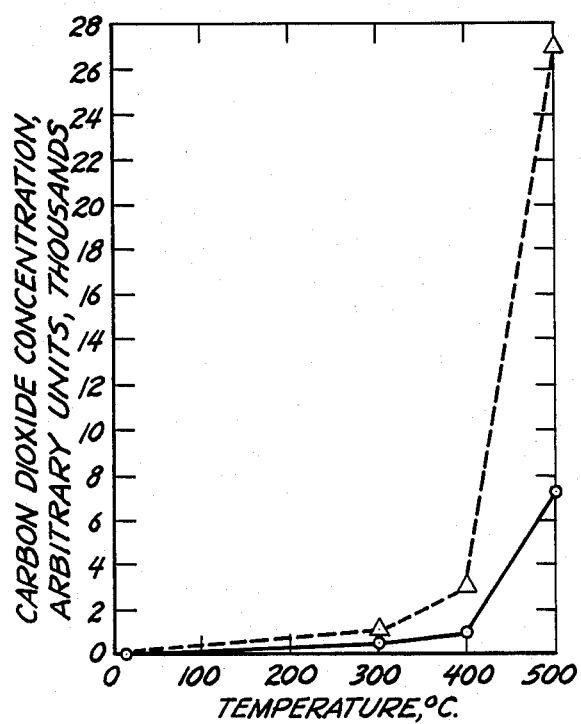
FIG. 3 is a graph of $CO_2$ production vs. temperature illustrating test results for good and bad samples.

FIG. 3 illustrates the results of actual experiments using the apparatus of FIG. 1. Carbon dioxide concentration is plotted versus temperature for two test coupons; the dashed line curve was obtained upon testing a coupon with cracks and an unsatisfactory oxidation resistance, and the solid line curve for a good coupon. The apparatus was tested for carbon contamination by heating it to 500° C. after an oxygen fill and the absence of carbon dioxide verified. The oven was programmed up from room temperature to 500° C. with intermediate stops at 300° C. and 400° C. Carbon dioxide measurements were made at room temperature, 300° C., 400° C. and 500° C. Immediately after the last measurement the oven was flooded with helium to protect the sample from further attack during the slow cooling of the oven.

The test of the unsatisfactory sample lasted about 3 hours and the carbon dioxide output shown by the dashed line drammatically rose from 0 to 27,483 arbitrary units at 500° C. The corresponding test of the good sample demonstrated significantly less carbon dioxide emission, increasing from 0 to only 7023 units. It was shown that the good sample had a minute amount of carbon loss and proves that this is a nondestructive test. There is a small amount of carbon dioxide emission even from the sample that passes the oxidation resistance test, and the threshold for unsatisfactory performance is set at a level that exceeds the emission from known acceptable samples. For this example a carbon dioxide concentration in the oven atmosphere greater than 12,000–16,000 arbitrary units signifies unsatisfactory oxidation resistance. The damage to the composite sample is not so serious, however, that it cannot be saved and reprocessed.

While the invention has been shown and described with reference to preferred embodiments thereof, it will be understood by those skilled in the art that various changes in form and details may be made without departing from the spirit and scope of the invention.

The invention claimed is:

1. A method of substantially non-destructively testing a carbon composite part for oxidation resistance, said part having a protective coating to inhibit destructive oxidation at an operating temperature greater than 2000° C., comprising:

heating said composite part in a sealed oven having an oxidizing atmosphere, to predetermined temperatures substantially below said operating temperature;

monitoring said atmosphere for carbon dioxide content during a heat cycle and measuring any carbon dioxide emitted by said part;

detecting a carbon dioxide concentration that exceeds an amount emitted by known acceptable parts and indicates said part has unsatisfactory oxidation resistance; and interrupting said heat cycle and flooding said oven with inert gas to prevent further oxidation so said part can be saved.

2. The method of claim 1 wherein said oxidizing atmosphere is pure oxygen.

3. The method of claim 1 wherein said oxidizing atmosphere is a mixture of oxygen and a gas having the same composition as said inert gas.

4. A method of substantially non-destructively testing a carbon composite part for oxidation resistance, said part having a protective coating to inhibit destructive oxidation at an operating temperature greater than 2000° 1 C., comprising:

heating said composite part to predetermined temperatures substantially below said operating temperature in a sealed oven filled with an oxidizing atmosphere;

collecting samples of the oven atmosphere and analyzing each sample for an amount of carbon dioxide emitted by said part;

determining that said part has unsatisfactory oxidation resistance by measuring a carbon dioxide concentration higher than a predetermined concentration level; and reducing the temperature of said oven and flooding with an inert gas to prevent further oxidation so said part can be saved.

5. The method of claim 4 wherein said predetermined temperatures to which said part is heated are below 500° C.

6. The method of claim 4 wherein the oven atmosphere sample is analyzed by a gas chromatograph.

7. The method of claim 6 wherein said gas chromatograph analyzes said sample for gaseous emissions from said part other than carbon dioxide.

8. A method of evaluating oxidation resistance of a sample of carbon-carbon composite having a protective coating to inhibit destructive oxidation at an operating temperature greater than 2000° C., comprising:

heating said composite sample to predetermined temperatures below said operating temperature in a sealed oven filled with an oxidizing atmosphere;

at selected times during a heat cycle, analyzing the oven atmosphere and measuring carbon dioxide emission from said part;

weighing said sample before and during said heat cycle and obtaining weight change measurements; and combining said carbon dioxide emission and weight change measurements to identify whether said carbon-carbon composite or coating has failed.

9. The method of claim 8 wherein said coating is silicon carbide and said weight change measurements and carbon dioxide emissions are employed to quantify changes in said carbon-carbon composite and silicon carbide coating.

10. The method of claim 8 wherein said oven atmosphere is analyzed by an instrument selected from the group consisting of a gas chromatograph, mass spectrometer and infrared detector.

* * * * *